July 7, 1970 MARIE LOUISE MEILLAND Plant Pat. 2,977
ROSE PLANT
Filed July 12, 1968
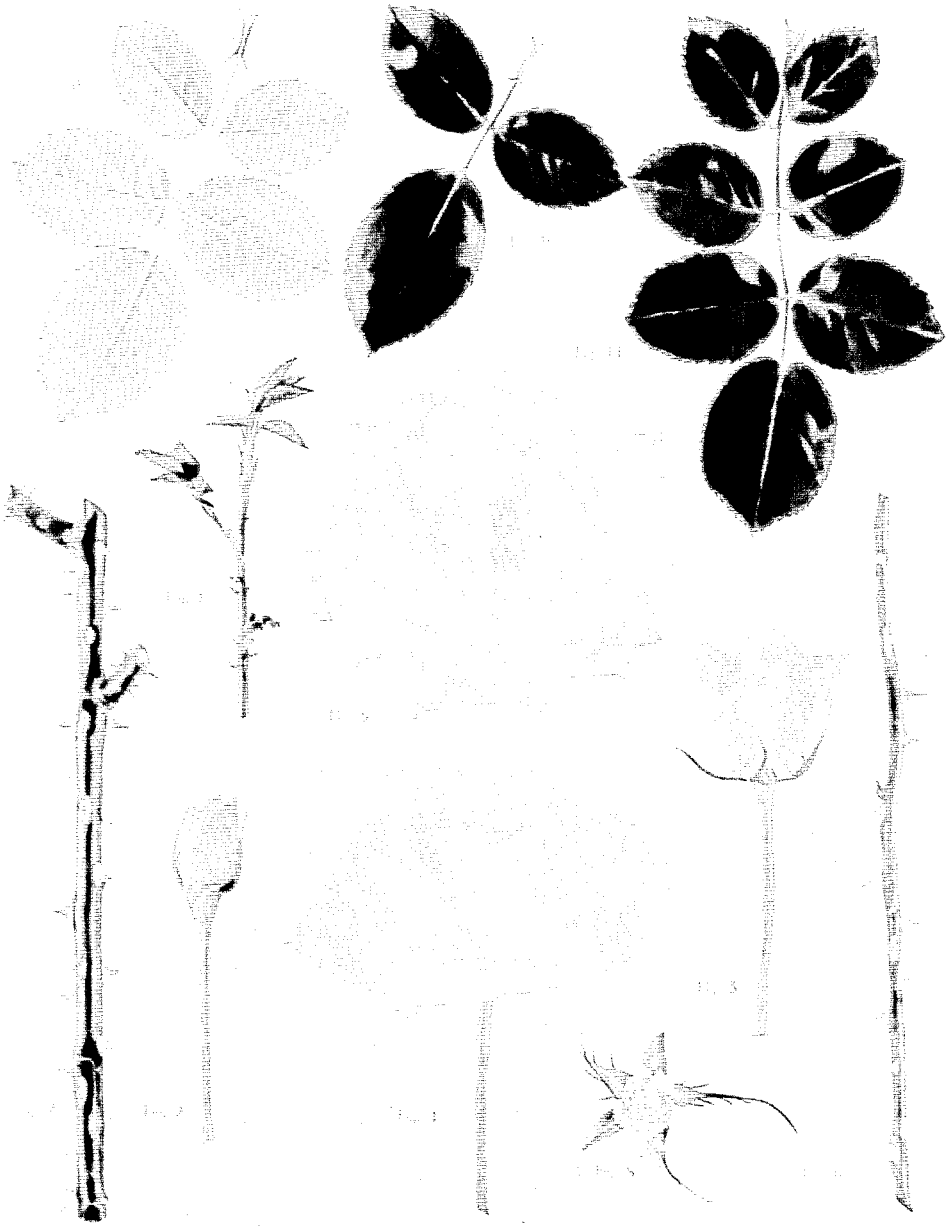

United States Patent Office

Plant Pat. 2,977
Patented July 7, 1970

2,977
ROSE PLANT

Marie Louise Meilland, Cap d'Antibes, Alpes-Maritimes, France, assignor to The Conard-Pyle Company, West Grove, Pa., a corporation of Pennsylvania Filed July 12, 1968, Ser. No. 744,593
Claims priority, application France, Aug. 7, 1967, 49,024
Int. Cl. A01h *5/00*
U.S. Cl. Plt.—17 1 Claim

ABSTRACT OF THE DISCLOSURE

A new and distinct variety of hybrid tea rose plant originated from crossing two unnamed varieties, one produced from crossing Baccara with White Knight, which was crossed on a variety obtained by crossing Baccara with Meibrem 172 F (Jolie Madame), and the other variety used as parent was obtained from crossing the variety Baccara with the variety Meibis 137 F (Paris-Match).

DESCRIPTION OF THE INVENTION

This invention relates to a new and distinct variety of rose plant of the hybrid tea class which was originated by me by crossing two unnamed varieties.

The object of the present invention is to create a variety of rose plant, of the hybrid tea class, with light Scarlet double flowers, which is distinguishable from varieties already known in that class and this kind of color, due to the following characteristics:

Purity and freshness of color of the flowers;
Unusual elegance of these flowers;
Very well suited to underglass culture for the production of long-stemmed cut flowers;
Suited just as well to growing in the open air, as a garden variety;
Development of a foliage more ample and more resistant to fungus diseases, particularly to powdery mildew.

Be cause of the above-mentioned characteristics, the present invention answers the needs of the horticultural industry for the production of cut flowers, as well as for all uses concerning the ornamentation of parks and gardens.

The aim that I had in view was to create a variety which would derive the aforementioned advantages through a genetic combination of two genitors whose previous respective study would allow me to expect, in their common progeny, the appearance of the characters sought for.

The rose chosen for female genitor (seed parent) came from the pollination of a yet unknown variety which had been obtained by crossing two varieties, also yet unknown, and resulting:

The first one, from the crossing of the variety generally known in the trade under the name of Baccara (Plant Pat. No. 1,367) and of the variety generally known in the trade under the name of White Knight (Plant Pat. No. 1,359).

The second one, from the crossing of the said variety Baccara and the variety Meibrem 172 F, more generally known in the trade under the name of Jolie Madame.

The rose chosen as male genitor (pollen) was an unknown variety obtained from crossing the variety Baccara and the variety Meibis 138 F, more generally known in the trade under the name of Paris-Match.

The operation of artificial pollination performed by me can therefore be expressed by the following schematic formula:

(Baccara × White Knight)
×
(Baccara × Meibrem 172 F Jolie Madame)
×
(Baccara × Meibis 138 F Paris-Match)

From the fruits formed by this controlled pollination, seeds were extracted, whose cells were the result of the combination of factors which existed in the cells of the genitors, and in virtue of which these genitors had been precisely chosen.

After having sown the above-mentioned seeds, I obtained 530 small plants, physically and biologically distinct from one another.

After having discarded all the small plants which were deficient or abnormal, or whose characters were too remote from the ones I was seeking, I proceeded with the grafting of the remaining plants, in order to carry on my work only on plants that were, in every respect, in conformity with those produced and commercialized by the professional nurserymen. I then undertook the selective study of the industrial plants thus formed. During this study, I was led to discard systematically all the rose plants which had been grafted, with the exception of one only which came the closest to the desired goal.

This rose plant had very elegant flowers; its light Scarlet color was very pure. Moreover, it was continuously producing long stems with an ample and especially healthy foliage.

Technical tests (grafting with started eye buds, dormant eye buds, on different understocks, in hot houses or cold greenhouses, in the open air, etc.) were then made in order to watch the behavior of the newly created variety. The results were conclusive and underlined the importance of creating this variety with a view to its industrial exploitation by horticulturists, for the production of cut flowers, and by the professional nurserymen for the ornamentation of parks and gardens.

The characters and properties of this new variety, obtained as indicated above, are thoroughly transmittable by agamic means, also called "asexual means," i.e. by any method of vegetative reproduction, and in particular by grafting an "eye" which will be called in the trade under the name of Meiretni 0593 F, and which will be found on industiral plants just as well as on cut stems delivered subsequently to the trade. Thus will be obtained once again the rose variety which is the object of the present invention, and whose botanical and descriptive characteristics are given below:

The accompanying drawing shows typical specimens of the flowers and foliage of my new variety in different stages of development and as depicted in color as nearly true as is reasonably possible to make the same in a color illustration of this character, and wherein:

FIG. 1 represents a specimen of young shoot;

FIG. 2 represents a specimen of a bud when the sepals start to open;

FIG. 3 represents a specimen of a bud when the first petals open;

FIG. 4 represents a specimen of flower in the course of opening;

FIG. 5 represents a specimen of a fully open bloom, flat view;

FIG. 6 represents a portion of a flowering stem;

FIG. 7 represents a portion of a main stem;

FIG. 8 represents a specimen of a receptacle, flat view, showing the disposition of the stamens and that of the pistills;

FIG. 9 represents a specimen of leaf with 3 leaflets (folioles) upper surface;

FIG. 10 represents a specimen of leaf with 5 leaflets, under surface;

FIG. 11 is a specimen of leaf with 7 leaflets, upper surface.

The following is a detailed description of my new variety with color terminology in accordance with the horticultural color chart of the Royal Horticultural Society:

(A) GREENHOUSE PLANTS

Class: Hybrid tea.

Plant: height—1m. 80 on an average; habit—erect.

Canes:

*Color.*—Young stems—Spinach Green (H.C.C. 187–0960/2). Mature wood—Spinach Green (H.C.C. 187–0960/1).

*Prickles.*—Shape—straight. Size—average. Quantity—average. Color: on young stems—yellowish green; on mature wood—Burnt Umber.

Leaves:

*Stipules.*—Normally adnate and pectinate—in general, fairly narrow and not much developed.

*Auricles.*—Fine; short; diverging.

*Petiole.*—Inside—the interior and the edges of the vein are reddish brown when the foliage is young; it is normal green in the mature foliage. Outside—light green, with, usually, one or several small, hooked prickles.

*Foliole.*—Number—3–5 and 7. Shape—elliptical. Serration—single; fairly even. Texture—leathery. Dimensions—ample; certain terminal folioles are from 8 to 9 cms. in length, and 5 to 6 cms. in width. General effect—dull foliage, of average thickness, and of exceptional dimensions. Color: upper surface—a little darker than Spinach Green (H.C.C. 187–0960); under surface—Lavender Green (H.C.C. 196–000761).

It should be noted that when growth starts, as also during vegetation, the foliage of the young shoots is Lettuce Green H.C.C. 176–861, with more or less reddish pigmentation on the edge of the folioles, either inside or outside.

Inflorescence:

*Number of flowers.*—Usually one flower to the stem.

*Peduncle.*—Very firm, with fairly numerous unsubstantial spines. It is about 10 cms. in length, on an average. It is Lettuce Green (H.C.C. 176–861).

*Sepals.*—Normal—slightly hairy and whitish green inside, fairly smooth and light green outside. Two out of five have a few small appendicles.

*Bud.*—Shape—pointed; slightly elongated. Size—medium. Color—when the first petal opens: the inside is Dutch Vermilion H.C.C. 156–717; the outside is slightly darker than Carmine Rose H.C.C. 75–621.

*Flower.*—Form—first of all turbinate, high-centered; then when open, protruding and imbricate petals, those of the exterior peripheray folding to a point.

*Double flower.*—Diameter—12 to 13 cms. Color—at the opening: inside—Scarlet H.C.C. 19–19; outside—Carmine Rose H.C.C. 75–621; when open: inside—Scarlet H.C.C. 19–19/1; outside—Carmine Rose H.C.C. 75–621/1; when full blown: inside—Porcelaine Rose H.C.C. 147–620; outside—Carmine Rose H.C.C. 75–621/1. Fragrance—very light tea odor. Duration—lasts a very long time.

*Corolla.*—Petals: texture—very firm and smooth. Shape—the petals of the exterior periphery are broadly rounded and bend to a point when the flower opens; the interior petals are also rounded but less developed and do not fold to a point; the central ones, near the stamens are usually dented and not always entire. Unguis—fairly well marked; it is Barium Yellow H.C.C. 131–503/2 and 503/1, with a white aureole. Number—40 on an average.

*Stamens.*—Number—150, average. Anthers—normal; yellowish. Filaments—fairly evenly placed; reddish.

*Pistils.*—Number—140 on an average. Stigmas—normal; yellowish. Styles—yellowish at base, then fuchsine up to the stigmas; they appear more or less strangled and twisted when coming out of the receptacle. Receptacle—normal; smooth; light green.

Development:

*Growth.*—Very vigorous vegetation.

*Tendency for recurrent bloom.*—Excellent.

*Resistance to diseases.*—Strong.

(B) GARDEN PLANTS

Plant: Height—Om. 65 on an average; habit—erect.

Foliage: Folioles—of lesser dimensions than those observed in the greenhouses; the texture is more leathery and not so dull.

Flower:

*Color.*—Same as in greenhouses, with however a more noticeable tendency towards Carmine Rose H.C.C. 75–621 than towards Porcelaine Rose H.C.C. 147–620 when full blown.

*Peduncle.*—Varying from 4 to 6 cms. in length. More or less reddish brown. Lasts a very long time.

Development:

*Resistance to spring frosts.*—Normal.

*Resistance to winter frosts.*—Very good.

*Resistance to diseases.*—Blackspot—very good. Mildew—very good. Rust—very good. Powdery mildew—especially good.

I claim:

1. A new and distinct variety of rose plant of the hybrid tea class, substantially as herein shown and described, characterized particularly in that the flower is double, light Scarlet, its petals are very firm and give the bloom first a turbinate form, which when open the petals are protruding and imbricate, those of the exterior periphery folding to a point; the plant is upright, with Spinach Green mature wood, or vigorous vegetation, has an excellent tendency for recurrent bloom, is very resistant to fungus diseases, its flowers last a very long time either on the plant or as a cut flower, and the petals drop off cleanly.

No references cited.

ROBERT E. BAGWILL, Primary Examiner